May 13, 1958 O. R. BRISTOW Plant Pat. 1,702
AZALEA PLANT
Filed March 1, 1957
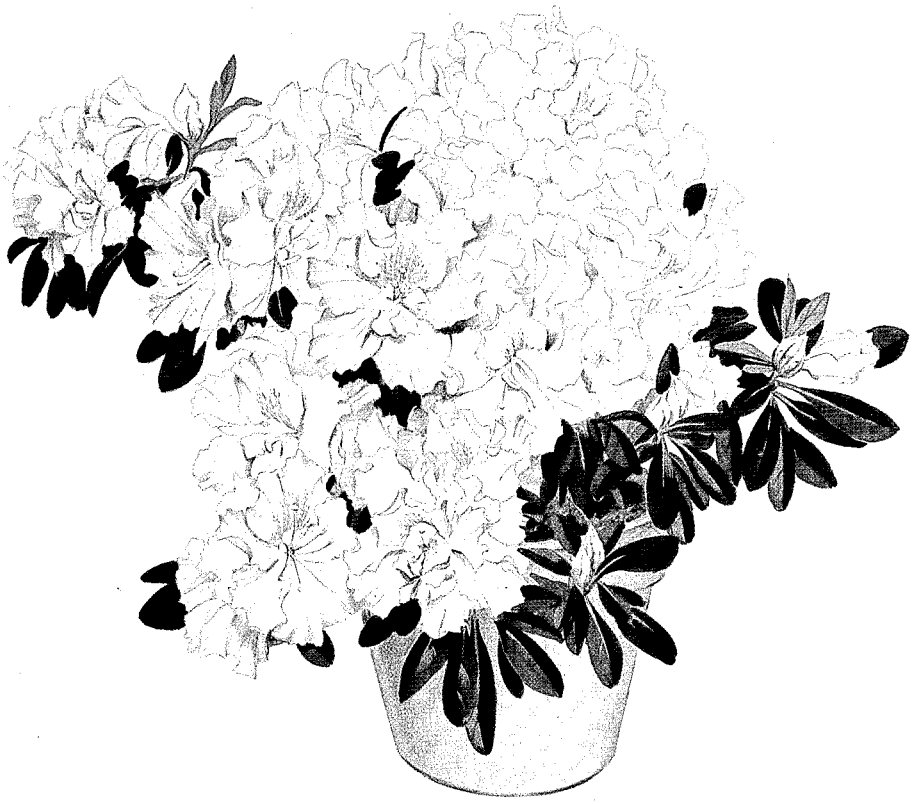
OWEN R. BRISTOW
INVENTOR.
BY Orville R. Seidner
AGENT United States Patent Office Plant Pat. 1,702
Patented May 13, 1958

1,702

AZALEA PLANT

Owen R. Bristow, San Bernardino, Calif., assignor to Mossholder Nursery, Orange County, Calif.

Application March 1, 1957, Serial No. 643,482

1 Claim. (Cl. 47—60)

This invention relates to a distinct and new variety of azalea plant reproduced as a result of deliberate experiments in hybridization carried out at my nursery in San Bernardino, California, the plant being derived from a cross-breeding of unpatented plants numbered 109B and 42 in my breeding records. This particular plant has been given the number 24A for identification purposes.

This distinct and new variety of azalea is particularly distinguished over known varieties by the appearance, color, and holding quality of the flower as well as its massive blooming habit.

The appearance and color of the flower will be noted in the accompanying illustration. Attention is invited to the exceptionally large size for a hose-in-hose type. It will also be noted that the flower is characterized by a ruffled or frilled edge, which together with the size of hose-in-hose bloom offer an exotic appearance not had by known azalea varieties.

The color and color markings of the flower together with behavior during the blooming period constitute an exceptional distinguishing characteristic. In this connection the flower has a very striking holding quality. The behavior of the bloom is characterized by the tendency to a gradual decrease in the soft salmon color saturation while at the same time increasing in brilliance during its long holding time.

The contrasting maroon speckling and throat markings do not change in saturation or brilliance to any substantial degree during the life of the flower, hence a particularly distinguishing characteristic of the flower over the usual varieties is the much brighter markings on the upper portion of the flower, giving it a very sensuous and luxurious appearance.

Asexual reproduction of this distinct and new variety of azalea was accomplished by me at my nursery in San Bernardino, California, by the known method of removing cuttings from the original hybrid plant which matured from a seedling, and potting the cuttings separately from the donor plant. Subsequent reproductions of the plant in the same manner indicate that the foregoing characteristics, as well as further distinguishing characteristics brought forth in the description below, are permanently fixed, and the accompanying illustration of a forced cutting grown plant in bloom shows the prolific blooming and striking color of the flowers.

The following is a detailed specification of the plant and flower, reference being had to the British Horticultural Chart of the British Colour Council for color identification of the flower and reproductive organs, and to the Plochere Color System for color identification of the foliage.

*Plant*

Form of plant: Bushy; symmetrical.
Growth habit: Fast, compact grower.
Rooting: Roots well; grows strongly on its own roots.

Blooming habit: Prolific bloomer both in glass house forced plants as well as outside blooming plants; flower holds on plant until faded to several shades lighter.
Blooming season: The normal outdoor heavy blooming season in southern California is in March; plant can be forced into bloom by mid-December; plant will bloom lightly outside from September to the heavy blooming season.
Suitability for forcing: Excellent.

*Foliage*

Size: Leaves average ¾" wide and 2" long.
Quantity: Abundant.
Color: New foliage—Plate #1121 on upperside, and Plate #1131 on underside; old foliage—Plate #1129 on upperside, and Plate #1130 on underside.
Shape: Oval, rounded on end.
Texture: Smooth.
Edge or margin: Normal.
Ribs and veins: Normal.
Aspect: Foliage has more of a flat green aspect than the usual glossy appearance.

*Flower*

Size: 3" across.
Flowers borne: Usually three on a stem.
Quantity of bloom: Abundant; massive.
Continuity: Long lasting flowers; good forcing variety.
Petalage:
*Size.*—1½" wide and 2" long.
*Number of petals under normal conditions.*—2 layers of petals, 5 petals on each layer with petaloids in center.
*Color of bud.*—Plate #621/1.
*Color of open flower.*—Plate #621/1 when open, with decreasing saturation after several days to #621/2. The upper ¼ of flower is speckled with color, Plate #826/3, starting at base of petals going out to within ¾" of the edge.
*Texture.*—Smooth.
Appearance: Massive blooms; soft salmon color with contrasting maroon speckling make this unique bloom an outstanding flower.
Shape: Hose-in-hose, characteristically ruffled or frilled; most flowers have center petaloids making them hose-in-hose semi-double.
Persistence: Sets heavy bud set each season.

*Reproductive organs*

Stamens: 9 or 10 on each flower except when petaloidy occurs, in which case the number of stamens is reduced.
*Anther.*—Normal.
*Filament.*—Off white, Plate #663/3.
Pollen: Pale yellow, Plate #604/2.
Style: White, Plate #63/3. Stigma—Light green, Plate #63, shiny.
Ovary: Normal.

Having illustrated and described the invention or discovery, what is claimed as new and patentable is:

A distinct and new variety of azalea plant, substantially as illustrated and described hereinabove, and characterized generally by the massive blooming habit of an unusually large hose-in-hose flower having ruffled edges, and further characterized by the extended holding quality of the flower, but particularly characterized by the flower color of a soft salmon with contrasting maroon speckling and throat markings.

No references cited.